United States Patent
Choi et al.

(10) Patent No.: US 7,959,616 B2
(45) Date of Patent: Jun. 14, 2011

(54) MEDICATED SLEEVE

(76) Inventors: Eugene Choi, Irvine, CA (US); Dong Hwan Choi, Suwon (KR); Mun Seok Han, Suwon (KR)

(*) Notice: Subject to any disclaimer, the term of this patent is extended or adjusted under 35 U.S.C. 154(b) by 0 days.

(21) Appl. No.: 12/317,568

(22) Filed: Dec. 27, 2008

(65) Prior Publication Data

US 2009/0118685 A1     May 7, 2009

Related U.S. Application Data

(63) Continuation of application No. 11/525,632, filed on Sep. 22, 2006, now Pat. No. 7,485,111.

(60) Provisional application No. 60/811,165, filed on Jun. 5, 2006, provisional application No. 60/845,710, filed on Sep. 19, 2006.

(51) Int. Cl.
*A61M 35/00* (2006.01)

(52) U.S. Cl. ........ 604/289; 604/327; 604/351; 604/396; 604/349; 604/347; 604/358; 604/365; 602/73; 602/70; 602/79; 427/2.1; 427/2.31

(58) Field of Classification Search .................. 604/289, 604/327, 351, 396, 349, 347, 358, 365
See application file for complete search history.

(56) References Cited

U.S. PATENT DOCUMENTS

| | | | |
|---|---|---|---|
| 3,097,644 A | 7/1963 | Parker | |
| 3,200,037 A | 8/1965 | Curtay et al. | |
| 3,232,291 A | 2/1966 | Parker | |
| 3,724,457 A | 4/1973 | Klatte | |
| 4,034,751 A | 7/1977 | Hung | |
| 4,674,489 A | 6/1987 | Lundy | |
| 4,878,908 A | 11/1989 | Martin et al. | |
| 5,064,653 A | 11/1991 | Sessions et al. | |
| 5,499,966 A | 3/1996 | Bulley et al. | |
| 5,503,908 A | 4/1996 | Faass | |
| 5,804,213 A | 9/1998 | Rolf | |
| 6,087,549 A | 7/2000 | Flick | |
| 6,290,663 B1 | 9/2001 | Darcey | |
| 6,548,728 B1 | 4/2003 | Faries, Jr. et al. | |
| D546,003 S | 7/2007 | Choi et al. | |
| 2004/0228803 A1 | 11/2004 | Smith et al. | |

FOREIGN PATENT DOCUMENTS

EP     0903131     3/1999

OTHER PUBLICATIONS

The American Heritage® Dictionary of the English Language, Fourth Edition copyright © 2000 by Houghton Mifflin Company.*

* cited by examiner

*Primary Examiner* — Tatyana Zalukaeva
*Assistant Examiner* — Ilya Y Treyger
(74) *Attorney, Agent, or Firm* — Kathleen L. Choi

(57) ABSTRACT

Embodiments of the invention provide a stretchable sleeve having a medicinal section that can be loaded with a medicinal composition and a perforated section comprising a plurality of openings, wherein the medicinal section and the perforated section overlap, and wherein the sleeve is sized so that the interior surface of the medicinal section comfortably fits a body portion and the medicinal section contacts the body portion at the site of pain. Embodiments of the invention also provide methods for preparing a sleeve by applying a medicinal composition to the inner surface of the medicinal section through the openings at the perforated section. Embodiments of the invention also provide methods for relieving pain in a body portion by pulling the sleeve in an outside-out configuration straight up a body portion without having to roll and flip its exterior surface outside.

18 Claims, 3 Drawing Sheets

MEDICATED SLEEVE

CROSS-REFERENCES TO RELATED APPLICATIONS

This application claims priority from and is a Continuation application of U.S. patent application Ser. No. 11/525,632, filed Sep. 22, 2006. This application also claims the benefit under 35 U.S.C. §119(e) of U.S. Provisional Application No. 60/811,165 filed on Jun. 5, 2006. This application also claims the benefit under 35 U.S.C. §119(e) of U.S. Provisional Application No. 60/834,710 filed on Aug. 1, 2006. The entire contents of each of the prior applications are hereby incorporated by reference.

BACKGROUND OF THE INVENTION

Various devices for applying medication through the skin are known in the art and are also commercially available. For example, minor muscle pains and arthritic pains can be relieved by applying patches containing topical analgesics (e.g., Tiger Balm patch, Bengay patch, and Icyhot® patch). When the site of pain is at or near a joint, the Icyhot® medicated sleeve manufactured by Chattem Inc. is particularly useful. This product is in the shape of a cylindrical sleeve made of a knitted fabric and has a region in the middle of the sleeve containing a menthol composition. Unlike medicated patches, sleeves provide extra flexibility and comfort when worn around joint areas.

While the Icyhot® medicated sleeve is a good product, it is somewhat complicated to manufacture and cumbersome to use. For example, these sleeves are manufactured and packaged in an inside-out configuration such that when a consumer opens a pouch, the inner surface of the sleeve is facing outward and is visible to the consumer. It appears that this inside-out configuration of the sleeve allows the manufacturer to apply a medicinal composition to the inner surface of the sleeve, which surface is intended to contact the skin. Then, on the pouch, the manufacturer provides illustrated directions for a consumer to initially pull up a sleeve in an inside-out configuration onto a leg or an arm, then roll and flip the sleeve into an outside-out configuration and contact the medicated area at the site of pain. This manufacturing process and directions for use for the Icyhot® medicated sleeve are complicated and cumbersome. Moreover, consumers may not even follow illustrated directions on the pouch and may pull the sleeve up straight in an inside-out configuration, thereby not receiving the full dose of a medication as intended by the manufacturer.

Therefore, there is a clear need in the art to overcome the above noted problems. Embodiments of the present invention provide solutions to these problems and meet other needs.

SUMMARY OF THE INVENTION

The present invention provides a medicated sleeve that is unique in design and function. The present sleeve can be pulled up straight, out of a pouch, without requiring a consumer to roll and flip its exterior surface outside. More specifically, the present invention relates to a stretchable sleeve having a first open end and a second open end, wherein the two open ends are interconnected by a passage surrounded by an interior surface of the sleeve, the sleeve comprising: (a) a medicinal section adapted to be loaded with a medicinal composition; and (b) a perforated section comprising a plurality of openings, wherein the medicinal section and the perforated section overlap, and wherein the passage of the sleeve is sized so that the interior surface of the sleeve contacts a body portion when the body portion is inserted into the passage of the sleeve through the open ends. Since the stretchable sleeves of the present invention are flexible and breathable, they are especially comfortable when worn around the joint areas as well as other areas of the body.

The present invention also relates to methods of preparing a sleeve of the invention by providing a sleeve in an outside-out configuration, applying a medicinal composition at the interior surface of the medicinal section through the openings at the perforated section of the sleeve, and packaging the sleeve in an outside-out configuration in a pouch.

The present invention further relates to a method of relieving pain in a body portion by pulling a sleeve of the present invention in an outside-out configuration straight up the body portion without having to roll and flip its exterior surface outside.

BRIEF DESCRIPTION OF THE DRAWINGS

FIG. 1b is a side plan view of the sleeve shown in FIG. 1a.

DETAILED DESCRIPTION OF THE INVENTION

Figure 1A:
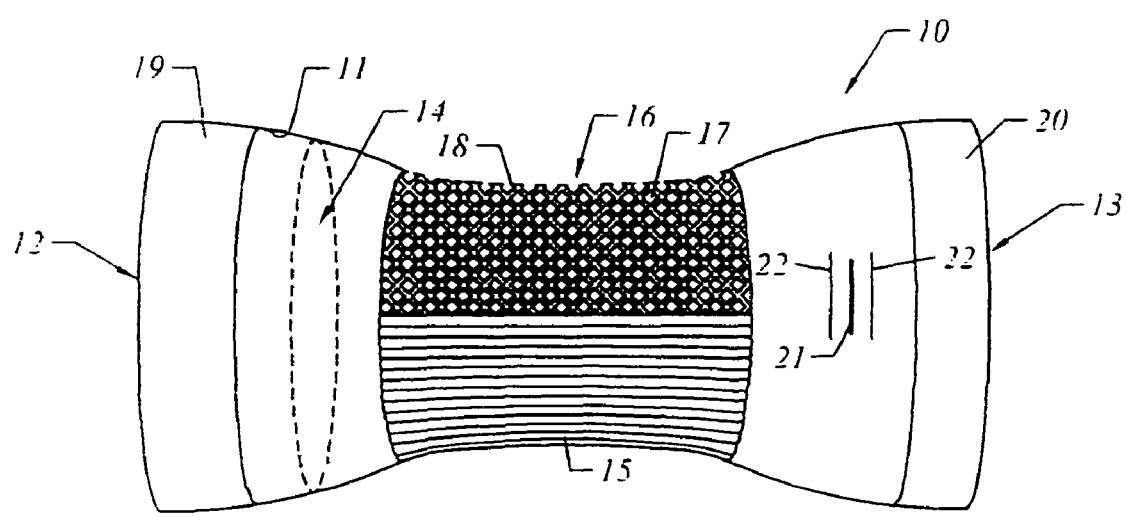
FIG. 1a is a top plan view of a sleeve according to one embodiment of the present invention.

The present invention provides a stretchable sleeve with unique features so that a sleeve need not be flipped inside out for a manufacturer to dose a medicinal composition to the interior surface of the sleeve. The present sleeves are manufactured and packaged in an outside-out configuration so that when a consumer opens a pouch, an outside or exterior surface of the sleeve is visible to the consumer. Therefore, a consumer can pull the present sleeve straight up, like a sock, out of a pouch and need not roll and flip the sleeve into an outside-out configuration as in the prior art. Manufacturing and packaging a sleeve in a correct configuration reduce a chance that a consumer may pull up the sleeve in a wrong configuration, thereby increasing the likelihood that a consumer will receive a maximum dose of a medicinal composition as intended by the manufacturer.

Generally, embodiments of the invention provide a sleeve comprising a medicinal section that is adapted to be loaded with a medicinal composition and a perforated section comprising a plurality of openings. In embodiments of the invention, the perforated section and the medicinal section are positioned in a sleeve so that at least portions of the two sections overlap. The term "overlap" can include a situation where at least a portion of the perforated section is capable of extending over and covering a part or all of the medicinal section, or vice versa. For example, when the passage of the sleeve is collapsed and the sleeve is flattened onto itself, the perforated section is capable of overlaying on top of the medicinal section. Depending on the size of each section, the locations of the two sections can vary. In one embodiment, the two sections may be located adjacent to each other in a sleeve. In another embodiment, the two sections may be located circumferentially opposite side of each other (e.g., if one were to look at a cross section of a sleeve that is cylindrical in shape, a midpoint of the medicinal section is located at one end of a diameter and a midpoint of the perforated section is located at the other end of the diameter). In yet another embodiment, the two sections may be adjacent to each other and also are located circumferentially opposite side of each other when the two sections occupy almost entire middle part of the sleeve as shown in FIGS. 1a-1c.

Because of the plurality of openings at the perforated section, a medicinal composition can be applied (e.g., by spraying) onto an interior surface of the medicinal section, through the openings of the perforated section, even though a sleeve is in an outside-out configuration. Therefore, a manufacturer need not have a sleeve in an inside-out configuration to apply a medicinal composition. Consequently, a consumer may open a pouch containing a sleeve in an outside-out configuration and pull the sleeve straight up his or her body portion, like a sock, without having to roll and flip the sleeve into a correct configuration as in the prior art.

Embodiments of the invention are further described by referring to the drawings. It is noted that the drawings are merely illustrative of embodiments of the invention and are not meant to limit the scope of the present invention in any way.

Figure 1B:
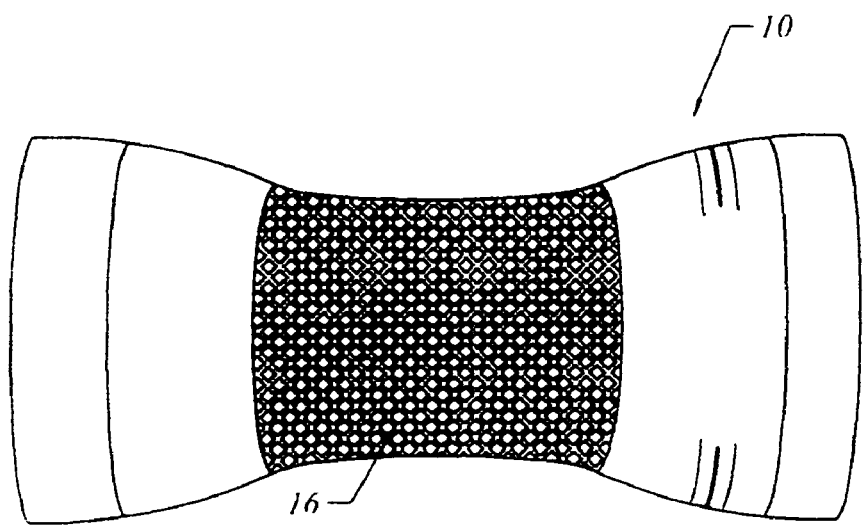
Figure 1C:
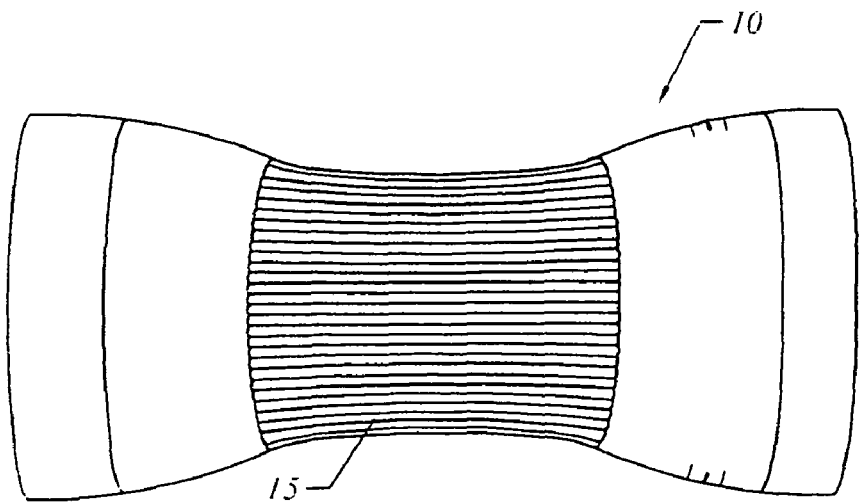
FIG. 1c is another side plan view of the sleeve shown in FIG. 1a, showing the opposite side of FIG. 1b.

Turning to the drawings, FIG. 1a shows a top plan view of a stretchable sleeve 10 according to one embodiment of the invention. The sleeve 10 is generally cylindrical or tubular in shape, and has a first open end 12 and a second open end 13. The two ends are interconnected by a passage 14 which is surrounded by an interior surface 11 of the sleeve 10. The passage 14 is large enough so that it can accommodate any suitable body portions, particularly joint areas such as an elbow, knee, wrist or ankle. The sleeve 10 may further comprise resilient bands 19 and 20 near open ends 12 and 13, respectively. In some embodiments, the bands 19 and 20 may be ribbed to provide additional resilience. The resilient bands 19 and 20 act like a garter to secure the sleeve at a desired body location and to minimize slipping of the sleeve during body movement.

The sleeve 10 can be made of any suitable material as long as it can be stretched to fit a body portion and has sufficient elasticity to contact the skin (particularly at the medicinal section 15) and to stay on the body portion. For example, it can be an elastic polymeric material, a woven, nonwoven or knitted fabric, or any combinations thereof. Preferably, the sleeve 10 is generally tubular or cylindrical in shape and is made of a knitted fabric. More preferably, the sleeve 10 is a seamless, circularly knitted sleeve so that it does not create any undesired crease on the skin when the sleeve is worn by a consumer for a prolonged period of time.

In an embodiment where a sleeve is made of knitted fabric, a variety of fibers may be used to prepare a sleeve. While the term "fiber" is used throughout the application, the "fiber" can mean a thread, filament or yarn as long as it can be used to knit a sleeve. In embodiments of the invention, the use of synthetic fibers is preferred over natural fibers, because synthetic fibers generally possess a better tensile strength. For example, synthetic fibers, such as polyamide, polyester or polyolefin, may be used in making a sleeve. The sleeve may further comprise spandex or other elastic fibers to provide additional stretchability and resilience.

The sleeves of the present invention can be produced in different dimensions (e.g., lengths and diameters) to accommodate different body portions and consumers of different sizes. For example, a sleeve designed for a knee area is generally larger in diameter and length than a sleeve designed for an elbow area. In general, the length of the sleeve in a relaxed state (i.e., an unstretched state prior to inserting a body portion) may range from about 5 cm to about to 40 cm, more preferably about 8 cm to about 30 cm, and even more preferably about 10 cm to about 25 cm. The diameter of the sleeve in a relaxed state may range from about 2 cm to about 15 cm, more preferably about 3 cm to about 10 cm, even more preferably about 4 cm to about 8 cm. Suitable combinations of different lengths or diameters for a sleeve can be readily determined by a manufacturer.

The sleeves of the present invention can also be produced to have different compression levels by selecting suitable materials and dimensions for a sleeve. For example, a compression level for a sleeve may vary from about 5 mmHg to about 60 mmHg. A sleeve having a compression level of about 5 mmHg to about 15 mmHg provides a light support like a regular pantyhose. A sleeve having a compression level of about 15 mmHg to about 20 mmHg provides a light to moderate compression, and it is useful in reducing mild swelling and fatigue of extremities. A sleeve having a compression level of about 20 mmHg to about 30 mmHg provides a moderate compression and provides relief from moderate varicosities with mild to moderate edema. A sleeve having a compression level of about 30 mmHg to about 50 mmHg provides a firm compression and provides relief from severe varicosities and severe edema. In a preferred embodiment, a sleeve has a compression level of about 5 mmHg to about 15 mmHg and fits a consumer's body portion snugly and comfortably.

In the middle part of the sleeve 10, the medicinal section 15 is located on one side, and the perforated section 16 that has a plurality of openings 17 is located on the other side as shown in FIG. 1a. In embodiments of the invention, the two sections 15 and 16 are positioned so that they overlap when the passage of the sleeve is collapsed and the sleeve is flattened onto itself. As shown in FIGS. 1a-c, the two sections are adjacent to each other and are located on the circumferentially opposite side of the sleeve and occupy almost entire middle part of the sleeve (e.g., about 40% to 60% of the surface area of the sleeve). FIG. 1b shows a side plan view of the sleeve 10 shown in FIG. 1a, showing mostly of the perforated section 16. FIG. 1c shows another side plan view of the sleeve 10 shown in FIG. 1a, showing mostly the medicinal section 15. The perforated section has a network of material 18, such as fibers, and interspaced therein are a plurality of openings 17.

The sizes of the medicinal section 15 and the perforated section 16 shown in FIGS. 1a-c are merely illustrative and may vary depending on the size of a body portion to be treated. For example, these two sections combined may occupy about 10% to about 90% of the surface area of the sleeve 10. In another example, these two sections may occupy about 20% to about 80% of the surface area of the sleeve 10. In yet another example, these two sections may occupy about 40% to 60% of the surface area of the sleeve 10. While the sizes of the two sections can be different, in a preferred embodiment, the size of the medicinal section 15 and the perforated section 16 are approximately the same. The similarity in size allows a manufacturer to apply a medicinal composition (e.g., via spraying) to the entire interior surface of the medicinal section through the openings at the perforated section.

In embodiments of the invention, the medicinal section 15 further comprises a reinforcing material in addition to the sleeve material. The reinforcing material may be of any suitable material and preferably has a low moisture absorbing property. If the reinforcing material were highly absorbent, then it may absorb the entire medicinal composition and may not release it to a body portion when a sleeve is worn by a consumer. For example, the reinforcing material may be synthetic fibers, such as polyester, nylon or polyolefin, or a synthetic foam that have a low moisture absorbing property. Preferably, the reinforcing material in the medicinal section 15 is made of secondary fibers that are different from primary fibers used to make the sleeve. In a preferred embodiment, the secondary, reinforcing fibers are terylene fibers. The reinforcing material may be colored differently than the rest of the sleeve to help a consumer locate an area of the sleeve that comprises a medicinal composition. For example, green, yellow or red fibers may be incorporated into the medicinal section 15, whereas the basic material for the sleeve is either white or skin-colored.

Any suitable active ingredients may be included in a medicinal composition in accordance with the present invention. For example, a medicinal composition may comprise one or more analgesics which provide pain relief. These include salicylates, menthol, camphor, eucalyptus oil, spearmint oil, or a combination thereof. In some applications, the medicinal composition can also include nonsteroidal anti-inflammatory drugs (NSAIs) such as salicylates or acetaminophen; steroidal anti-inflammatory (SAI) agents such as hydrocortisone; anesthetic agents such as benzocaine or lidocaine; or rubefacient agents such as capsicum.

In a preferred embodiment, a medicinal composition comprises menthol or its derivative as an active ingredient. An effective concentration of an active ingredient may vary depending on the selection of a particular active ingredient. For example, a medicinal composition may comprise menthol at a concentration of from about 1% to about 50%, from about 5% to about 30%, or from about 10 to about 20%, by weight of the composition. In certain embodiments, a medicinal composition comprises 16% menthol by weight of the composition. A sleeve comprising an analgesic, such as menthol, as an active ingredient is particularly useful in alleviating minor aches and pains of muscles and joints associated with arthritis, muscle strain, bruises and sprains.

In addition to an active ingredient, a medicinal composition typically comprises at least one excipient such as preservatives, antioxidants, moisturizers, emollients, buffering agents, solubilizing agents, penetration enhancers, and skin protectants. Ideal compositions for use as topical medicinal composition should disperse easily onto the skin and deliver their active ingredients in a way that allows a portion to penetrate the skin rapidly, for prompt relief, while also maintaining an active reservoir on the surface of the skin to provide sustained relief. Ideally, the composition is formulated to enable neat and easy application with a minimal chance of staining clothes. Suitable excipients in a topical medicinal composition are well-known in the art (see, e.g., M. Ramchandani and R.

Toddywala, "Formulation of Topical Drug Delivery Systems" in Transdermal and Topical Drug Delivery Systems, pp. 539-92 (T. K. Ghosh, W. R. Pfister and S. Yum, Eds. 1997), which is hereby incorporated by reference in its entirety).

As shown in FIGS. 1a-c, the sleeve 10 has the perforated section 16 comprising a plurality of openings 17. In one embodiment, the openings 17 may be produced by burning a plurality of discrete holes through the sleeve material in the perforated section 16. In another embodiment, the perforated section 16 is like a mesh which is integral with the rest of the sleeve 10. For example, the perforated section 16 has a mesh or a network of fibers 18 with evenly spaced openings 17 in a sleeve made of knitted fabric. In a preferred embodiment, the perforated section 16 is an integral part of the knitted fabric that is more loosely knitted than the rest of the sleeve 10. In this instance, the openings 17 in the perforated section 16 may be produced by changing a program for a knitting pattern in an automatic weaving machine.

The openings 17 in the perforated section 16 can be of any suitable shape and size as long as they are large enough to pass droplets of a medicinal composition. For example, the openings may be in the shape of a circle, oval, triangle, square, rectangle or diamond. In embodiments of the invention, the perforated section 16 is in the shape of a mesh with diamond shaped openings 17. Also, the size of openings may vary. For example, each opening may be about 0.3 mm to 3 cm in its longest dimension (e.g., diameter) in a relaxed state of the sleeve prior to inserting a body portion. In embodiments of the invention, each opening may be about 1 mm to 2 cm, more preferably about 2 mm to 1 cm in diameter, in a relaxed state of the sleeve prior to inserting a body portion through the sleeve.

In embodiments of the invention, one or more short lines 21 of different colored fiber (e.g., black) may be incorporated near the open ends 12 or 13 of the sleeve. These lines are designed to guide a consumer to cut a hole in a sleeve for a thumb or a big toe in the event that the site of pain is at a wrist or ankle. The insertion of a thumb or a big toe into a hole in a sleeve may assist in stabilizing the sleeve at the wrist or ankle. The areas 22 shown in FIG. 1a near the colored line 21 are reinforcement lines around the colored line 21 to prevent further ripping when a consumer cuts a hole at the line 21.

A stretchable sleeve of the present invention may be prepared in many different ways, depending on the base material that is used to make the sleeve. For example, if a sleeve is made of an elastic polymeric material, a seamless tubular material may be extruded from an extrusion machine. The tubular material can then be cut into an appropriate length to produce a sleeve suitable for enclosing a body portion. The perforated section may be produced in a mid-section of the extruded tubular material by burning holes (e.g., via laser), or by punching holes mechanically (e.g., needle-punching). The medicinal section may be incorporated using a suitable material such as foam, pads or fabric.

In a preferred embodiment, a stretchable sleeve of the present invention is made of a knitted fabric and may be produced using an automatic weaving machine. Various automatic weaving machines such, as circular knitting machines, are known in the art. Generally, weaving interlaces the weft threads (the horizontal threads) and the warp threads (lengthwise, or perpendicular to the weft) on a loom, while knitting intertwines fiber or thread in a continuous series of connected needle loops on a machine. The automatic weaving machines are usually equipped with a patterning control device. As such, a mesh-like pattern on the perforated section 16 can be inserted at appropriate times during the knitting of the sleeve. The size of the holes and their shape in the perforated section 16 may be pre-programmed. The medicinal section 15 can also be reinforced with secondary fibers at appropriate time during the knitting of the sleeve.

Once the sleeve 10 is manufactured, a medicinal composition can be applied onto the medicinal section of the sleeve. In one embodiment, the sleeve (in an outside-out configuration with its exterior surface facing outward) may be collapsed onto itself on a flat surface with the perforated section 16 facing the top and the medicinal section 15 facing the bottom. In this configuration, a medicinal composition may be applied (e.g., by spraying from an injection nozzle) from the top onto the interior surface of the medicinal section 15 through the openings at the perforated section 16. This process allows the interior surface of the medicinal section to have the highest concentration of a medicinal composition, without having to flip the sleeve inside out prior to applying a medicinal composition.

In some embodiments, subsequent to applying a medicinal composition, the prepared sleeve may be flattened as shown in FIG. 1a, so that the interior surface of the medicinal section is flatly collapsed against itself. Then the collapsed sleeve may be folded in one half lengthwise. The folded sleeve may then be positioned between a folded plastic support. The folded sleeve inside the folded plastic support can be inserted and sealed in an air-tight pouch to prevent evaporation of a medicinal composition.

Figure 2A:
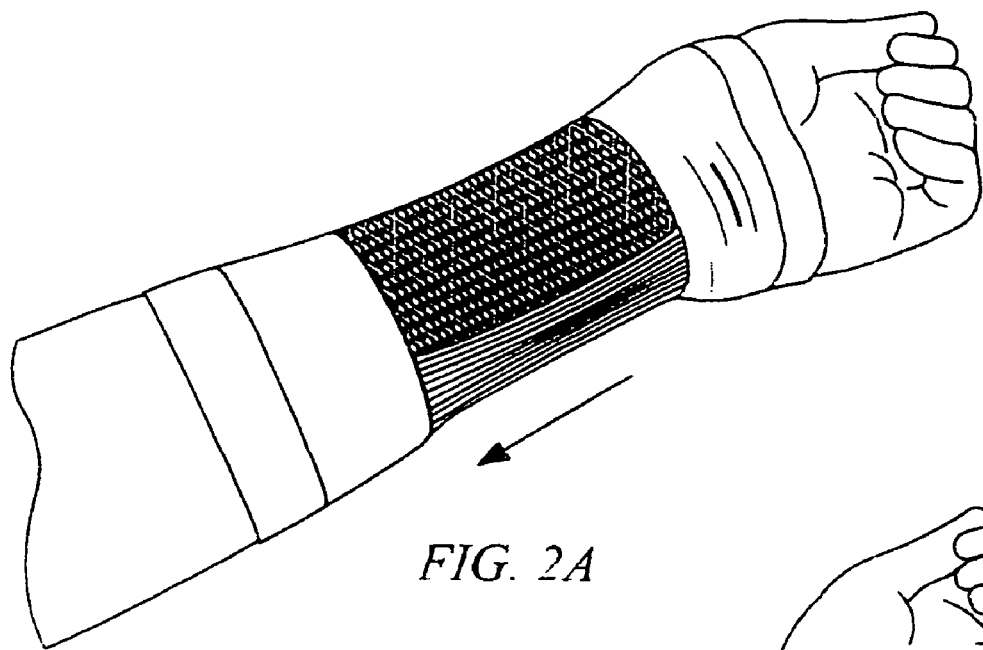
FIGS. 2a and 2b show a process of applying a sleeve around an elbow.
Figure 2B:
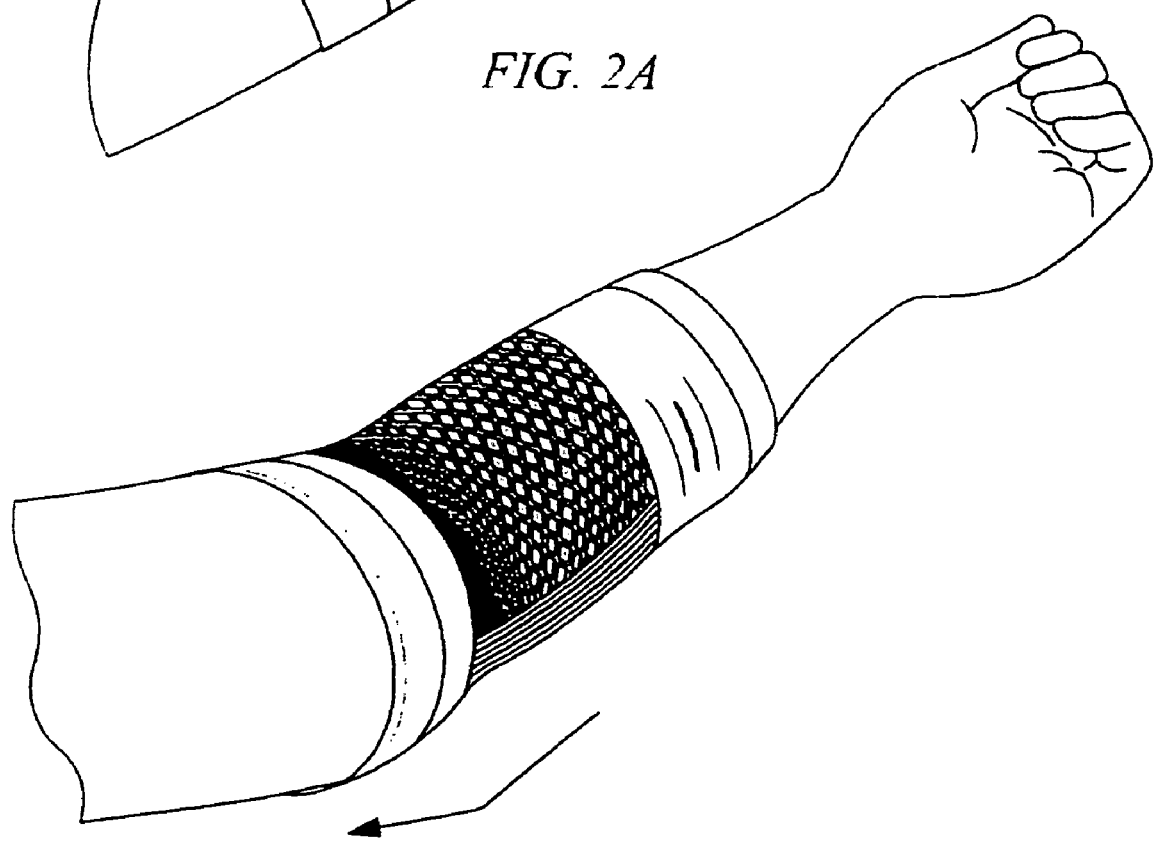

Now turning to FIGS. 2a and 2b, a consumer can open a pouch and pull the sleeve 10 straight up an arm (or any other body portion), like a sock, since the sleeve is packaged in an outside-out configuration. Then a consumer may position the interior surface of the medicinal section 15 at a site of a body portion where a relief of pain is desired (e.g., at an elbow). There is no need for a consumer to roll and flip the sleeve outside-out as in the prior art. The production and packaging of a sleeve in an outside-out configuration also increases the likelihood that a consumer will pull up a sleeve in a correct configuration without reading any instructions on the packaging and receive a full dosage of a medicinal composition.

Figure 3A:
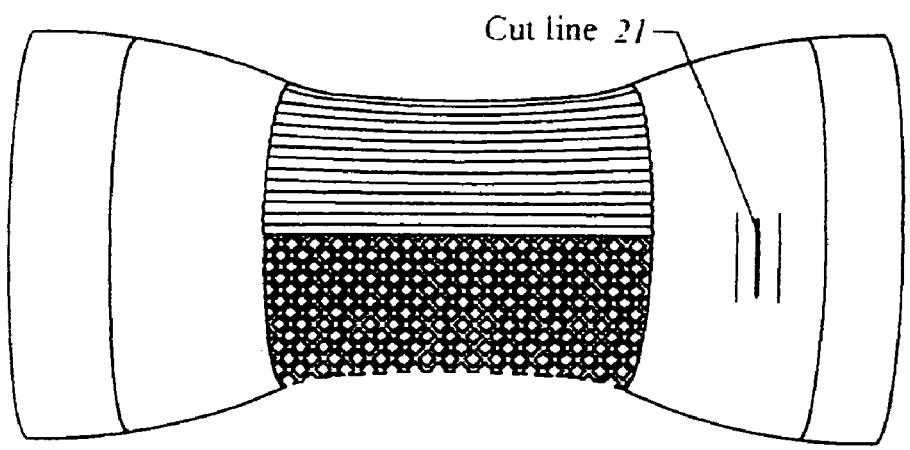
FIG. 3a shows a sleeve with a line which can be cut to insert a thumb or a big toe.
Figure 3B:
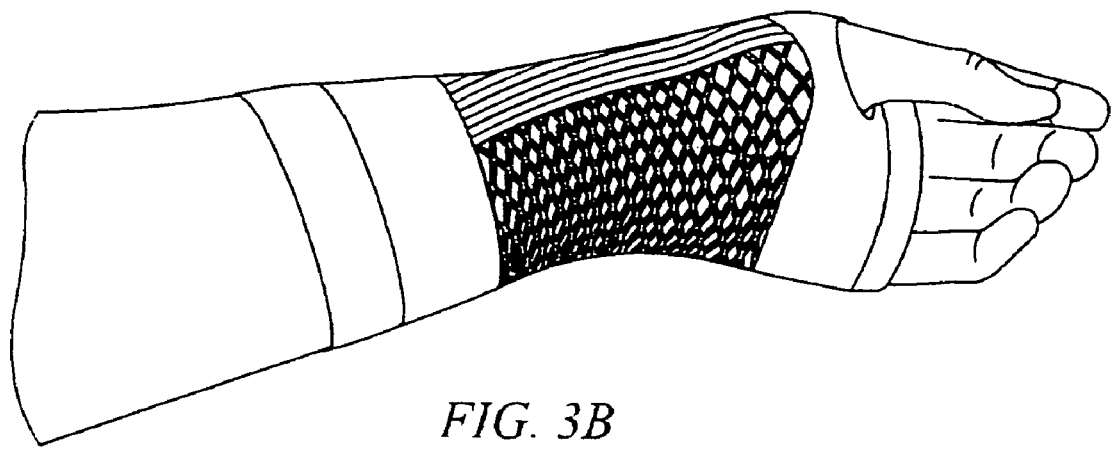
FIG. 3b shows a sleeve which has been cut to create a thumb hole so that it can be applied around a wrist.

FIGS. 3a illustrates line 21 that may be cut to create a hole to insert a thumb or big toe. As shown in FIG. 3b, after a hole is cut in the sleeve at line 21, a thumb can be inserted into the hole, and then a sleeve can be pulled up and securely applied around a wrist.

EXAMPLE

Using an automatic weaving machine, a sleeve was woven with 70% polyamide fiber, 20% spandex fiber and 10% colored terylene fiber.

A medicinal composition was prepared using the following formulation:

| Active Ingredient | |
|---|---|
| Menthol [KP] | 16.0% |
| Inactive ingredient | |
| diethylene glycol monoethyl ether [NF] | 4.00% |
| diisopropyl adipate [KSCI] | 10.00% |
| EDTA-2Na [KP] | 0.10% |
| cabomer [NF] | 0.35% |
| glycerin [KP] | 3.00% |
| polysorbate80 [KSCI] | 2.00% |
| ethanol [KP] | 5.00% |
| cethyl alcohol [KP] | 1.00% |
| glyceryl stearate [KP] | 0.50% |
| aloe vera gel [KSCI] | 0.50% |
| PEG-150 distearate [KSCI] | q.s |
| sodium hydroxide [KSCI] | q.s |
| methyl paraben [KP] | 0.15% |
| water [KP] | q.s |

KSCI: Korea Standard of Cosmetic Ingredients
KP: Korea Pharmacopoeia
% by weight of the composition The above ingredients were mixed together to prepare a medicinal composition in a lotion form. For each sleeve, 2 grams of the medicinal composition was spread to the interior surface of the medicinal section in the sleeve using an injector system. The sleeve was packaged in an air-tight aluminum pouch.

It is understood that the examples and embodiments described herein are not intended to limit the scope of the invention. Various modifications, alternative constructions and equivalents may be employed without departing from the scope of the appended claims. Moreover, one or more features of any embodiments may be combined with any other feature of any other embodiment in any manner without departing from the scope of the present invention.

All publications, patents and patent applications cited herein are hereby incorporated by reference for all purposes in their entirety.

What is claimed is:

1. A stretchable sleeve having a first open end and a second open end, wherein the two open ends are interconnected by a passage surrounded by an interior surface of the sleeve, the sleeve comprising:
   (a) a medicinal section adapted to be loaded with a medicinal composition; and
   (b) a perforated section comprising a plurality of openings, each opening having a dimension of about 1 mm to about 2 cm in a relaxed state of the sleeve,
   wherein the medicinal section and the perforated section are two discrete sections which are located on circumferentially opposite sides of the sleeve and only the perforated section has the plurality of openings in the sleeve,
   wherein the medicinal section and the perforated section overlap when the passage of the sleeve is collapsed and the sleeve is flattened onto itself,
   wherein the passage of the sleeve is sized so that the interior surface of the sleeve contacts a body portion when it is inserted into the passage of the sleeve through the open ends,
   wherein the medicinal section further comprises a reinforcing material made of secondary fibers that are different from primary fibers used to make the sleeve, and
   wherein the reinforcing material is colored differently than the rest of the sleeve.

2. The sleeve of claim 1, wherein the medicinal section and the perforated section together occupy about 40 percent to about 60 percent of the surface area of the sleeve.

3. The sleeve of claim 1, wherein the sleeve is made of a knitted fabric and the perforated section is an integrated part of the knitted fabric that is more loosely knitted than the rest of the sleeve.

4. The sleeve of claim 1, wherein the medicinal section is loaded with a medicinal composition comprising a menthol.

5. The sleeve of claim 3, wherein the medicinal composition is applied to the interior surface of the medicinal section through the openings of the perforated section of the sleeve.

6. The sleeve of claim 1, wherein the sleeve is made of a knitted fabric.

7. The sleeve of claim 6, wherein the medicinal section comprises a reinforcing material having a low moisture absorbing property.

8. The sleeve of claim 7, wherein the reinforcing material is made of terylene fibers.

9. The sleeve of claim 6, wherein the medicinal section is loaded with the medicinal composition comprising an analgesic as an active ingredient.

10. The sleeve of claim 9, wherein the active ingredient is a menthol.

11. The sleeve of claim 10, wherein the perforated section is in the form of a mesh.

12. The sleeve of claim 6, wherein the perforated section is an integral part of the knitted fabric that is more loosely knitted than the rest of the sleeve.

13. The sleeve of claim 1, wherein the medicinal section and the perforated section of the sleeve are about the same size.

14. The sleeve of claim 6, wherein the sleeve comprises a resilient hand around at least one open end of the sleeve to assist securing the sleeve around the body portion.

15. The sleeve of claim 6, wherein the sleeve has a compression level between about 5 mmHg to about 15 mmHg.

16. A method of preparing a stretchable sleeve, the method comprising:
(a) providing the sleeve in an outside-out configuration, the sleeve having a first open end and a second open end, wherein the two open ends are interconnected by a passage surrounded by an interior surface of the sleeve, the sleeve comprising: (i) a medicinal section adapted to be loaded with a medicinal composition; and (ii) a perforated section comprising a plurality of openings, each opening having a dimension of about 1 mm to about 2 cm in a relaxed state of the sleeve, wherein the medicinal section and the perforated section are two discrete sections which are located on circumferentially opposite sides of the sleeve and only the perforated section has the plurality of openings in the sleeve, wherein the medicinal section and the perforated section overlap when the passage of the sleeve is collapsed and the sleeve is flattened onto itself, wherein the passage of the sleeve is sized so that the interior surface of the sleeve contacts a body portion when it is inserted into the passage of the sleeve through the open ends, and wherein the medicinal section further comprises a reinforcing material made of secondary fibers that are different from primary fibers used to make the sleeve, and wherein the reinforcing material is colored differently than the rest of the sleeve; and
(b) applying the medicinal composition to the interior surface of the sleeve at the medicinal section through the openings at the perforated section of the sleeve.

17. The method of claim 16, wherein the sleeve is made of a knitted fabric wherein the perforated section is an integral part of the knitted fabric that is more loosely knitted than the rest of the sleeve, and the medicinal section includes low moisture absorbing secondary fibers.

18. The method of claim 17, wherein the medicinal composition comprises menthol as an active ingredient.

* * * * *